(12) United States Patent
Pai et al.

(10) Patent No.: US 11,547,323 B2
(45) Date of Patent: Jan. 10, 2023

(54) PATIENT MODEL ESTIMATION FROM CAMERA STREAM IN MEDICINE

(71) Applicant: Siemens Healthcare GmbH, Erlangen (DE)

(72) Inventors: Santosh Pai, Plainsboro, NJ (US); Klaus Kirchberg, Plainsboro, NJ (US); Vivek Singh, Princeton, NJ (US); Ruhan Sa, Monmouth Junction, NJ (US); Andreas Wimmer, Forchheim (DE); Ankur Kapoor, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 456 days.

(21) Appl. No.: 16/791,196

(22) Filed: Feb. 14, 2020

(65) Prior Publication Data
US 2021/0251516 A1 Aug. 19, 2021

(51) Int. Cl.
| | |
|---|---|
| *A61B 5/107* | (2006.01) |
| *G06T 7/246* | (2017.01) |
| *G06T 7/73* | (2017.01) |
| *G16H 40/67* | (2018.01) |
| *A61B 5/00* | (2006.01) |
| *G06T 17/20* | (2006.01) |
| *G06V 40/10* | (2022.01) |
| *A61B 5/055* | (2006.01) |
| *A61B 6/04* | (2006.01) |
| *A61N 5/10* | (2006.01) |

(52) U.S. Cl.
CPC .......... *A61B 5/1079* (2013.01); *A61B 5/0077* (2013.01); *A61B 5/1077* (2013.01); *G06T 7/246* (2017.01); *G06T 7/73* (2017.01); *G06T 17/20* (2013.01); *G06V 40/10* (2022.01); *G16H 40/67* (2018.01); *A61B 5/055* (2013.01); *A61B 6/0492* (2013.01); *A61B 2576/00* (2013.01); *A61N 2005/1059* (2013.01); *G06T 2207/10028* (2013.01); *G06T 2207/30196* (2013.01)

(58) Field of Classification Search
USPC .................. 382/154, 103, 128, 278; 600/476
See application file for complete search history.

(56) References Cited

U.S. PATENT DOCUMENTS

| | | | |
|---|---|---|---|
| 9,524,852 B2 | 12/2016 | Tian | |
| 2005/0203373 A1* | 9/2005 | Boese | G06T 7/38 600/407 |

(Continued)

FOREIGN PATENT DOCUMENTS

EP 3406196 A1 11/2018

OTHER PUBLICATIONS

U.S. Appl. No. 16/283,864, filed Feb. 25, 2019.
(Continued)

*Primary Examiner* — Kathleen Y Dulaney

(57) ABSTRACT

For patient model estimation from surface data in a medical system, a stream or sequence of depth camera captures are performed. The fitting of the patient model is divided between different times or parts of the sequence, using the streaming capture to distribute processing and account for patient movement. Less manual involvement may be needed due to the regular availability of image captures. Subsequent fitting may benefit from previous fitting.

15 Claims, 5 Drawing Sheets

(56) References Cited

U.S. PATENT DOCUMENTS

| | | | |
|---|---|---|---|
| 2008/0212858 A1* | 9/2008 | Boese | G06T 7/38 |
| | | | 382/130 |
| 2009/0018435 A1* | 1/2009 | Hsieh | A61B 6/032 |
| | | | 600/425 |
| 2012/0169333 A1* | 7/2012 | Katscher | G06T 7/246 |
| | | | 324/301 |
| 2017/0112416 A1* | 4/2017 | Hao | A61B 6/032 |
| 2017/0220709 A1* | 8/2017 | Wan | A61N 5/1048 |
| 2017/0249423 A1 | 8/2017 | Wang et al. | |
| 2017/0311841 A1 | 11/2017 | Rothgang | |
| 2018/0140270 A1* | 5/2018 | Profio | A61B 6/0407 |
| 2018/0158192 A1* | 6/2018 | Rocque | A61B 5/0075 |
| 2018/0289574 A1* | 10/2018 | Hiratsuka | A61B 5/055 |
| 2019/0069856 A1* | 3/2019 | Achkire | A61B 6/022 |
| 2019/0206051 A1* | 7/2019 | Cao | A61B 5/1077 |
| 2020/0049785 A1* | 2/2020 | Liu | G06T 7/254 |
| 2020/0051239 A1* | 2/2020 | Braun | G01R 33/543 |
| 2020/0206536 A1* | 7/2020 | Wang | G06T 7/246 |
| 2020/0258243 A1* | 8/2020 | Chang | A61B 5/107 |
| 2020/0268251 A1* | 8/2020 | Hao | A61B 5/055 |
| 2020/0268339 A1* | 8/2020 | Hao | A61B 6/0492 |
| 2020/0375546 A1* | 12/2020 | Shoudy | A61B 5/7425 |
| 2021/0098112 A1* | 4/2021 | Gagnon | G16H 50/20 |
| 2021/0366202 A1* | 11/2021 | Xu | G06F 3/147 |
| 2022/0020164 A1* | 1/2022 | Wang | G06T 7/30 |

OTHER PUBLICATIONS

Singh, Vivek, et al. "Estimating a patient surface model for optimizing the medical scanning workflow." International Conference on Medical Image Computing and Computer-Assisted Intervention. Springer, Cham, 2014.

\* cited by examiner

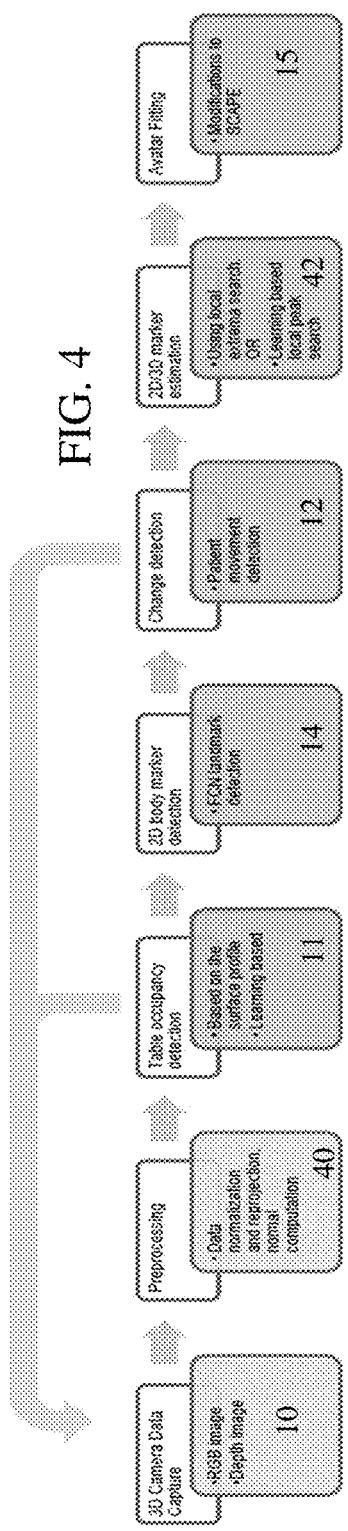
FIG. 4
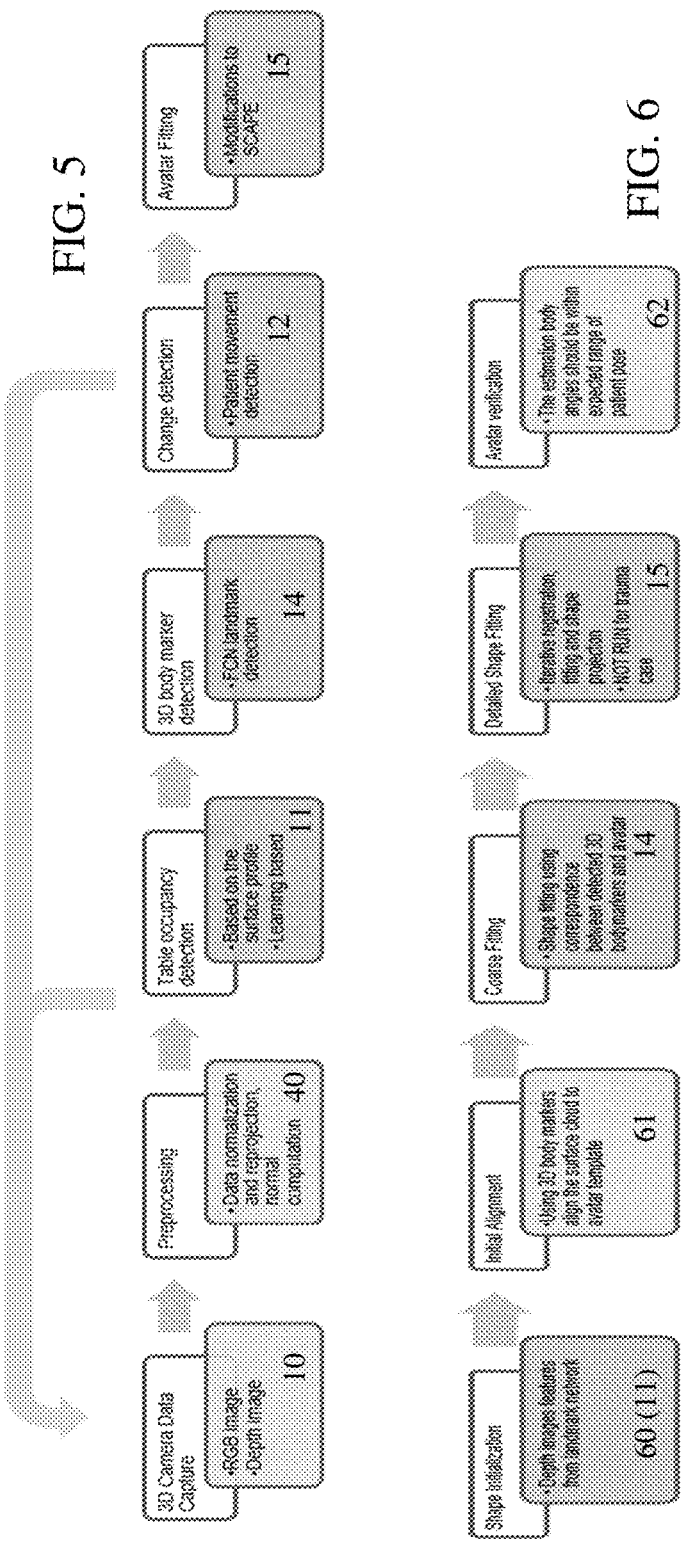
FIG. 5
FIG. 6

PATIENT MODEL ESTIMATION FROM CAMERA STREAM IN MEDICINE

BACKGROUND

The present embodiments relate to medical therapy or imaging. A medical system is configured by a medical professional based on the patient position relative to the medical system. Improper patient positioning may cause problems. For example, the quality of medical images acquired from a computed tomography (CT) scanner is best when images are acquired with iso-center of body region of the patient aligned to the origin of the gantry.

Manual positioning may be unreliable (error prone) and time consuming. Automatic patient positioning uses a single RGBD snapshot (planning image) of the patient to detect body landmarks and to fit an avatar to the patient. The avatar is used to set the (horizontal and vertical) table position for a body region to be scanned. The radiographer triggers the snapshot manually and may manually move the bed or patient. The patient pose may change after the snapshot is taken, such as the patient moving to accommodate a head rest or knee rest insertion, thus invalidating the planning image. This problem may be partially solvable by triggering another snapshot manually when the patient pose changes. Scan preparation time is increased by repeating the snapshot. The radiographer workload is increased, and the patient may have a resulting un-pleasant experience.

SUMMARY

Systems, methods, and computer readable media are provided for patient model estimation from surface data in a medical system. A stream or sequence of depth camera captures are performed. The fitting of the patient model is divided between different times or parts of the sequence, using the streaming capture to distribute processing and account for patient movement. Less manual involvement may be needed due to the regular availability of image captures. Subsequent fitting may benefit from previous fitting.

In a first aspect, a method is provided for patient model estimation from surface data in a medical system. A three-dimensional camera captures a stream of the surface data representing an outer surface of a patient at different times including a first time and a second time. The first time is earlier than the second time. The patient model is fit in a first way to the surface data of the first time. The patient is monitored for a change in patient position. The patient model is fit in a second way to the surface data of the second time. The second way is different than the first way and uses results of the fitting of the patient model in the first way. The fitting in the second way is performed when the patient position is maintained. A bed position of a bed of the medical system is adjusted based on the fitting of the patient model in the second way.

In one embodiment, the three-dimensional camera is a depth sensor. The capturing and fitting in the first and second ways may occur without user input relative to any camera images from the surface data.

Various ways or types of fitting may be used. For example, the first way is fitting model landmarks to landmarks detected from the surface data of the first time, and the second way is fitting a three-dimensional mesh to the surface data of the second time. The results from the first way may be used to initialize or constrain the fitting of the second way. For example, the second way uses the results by initializing the fitting of the three-dimensional mesh from the fitting of the model landmarks to the detected landmarks.

In another embodiment, the patient is detected on the bed from surface data of the stream from an earlier time than the first time. The fitting of the patient model in the first way and the monitoring are activated in response to the detecting of the patient.

In other embodiments, the bed is adjusted so that a center of the patient from the patient model fit in the second way is at an iso-center of the medical system. The embodiments may include adjusting the bed position without user input of the bed position.

In an embodiment, the monitoring continues after the fitting to the surface data of the second time. The fitting in the second way is repeated using the surface data from a third time after the second time in response to a variation in the patient position. The bed position is updated based on results of the repetition of the fitting in the second way. The repetition of the fitting in the second way may be constrained, such as constraining the fitting to a region of interest. In any fitting, constraints may be used. For example, the fitting in the second way is a fitting with constraints for the bed position and constraints for non-patient objects.

In one embodiment, the fitting in the first way is a two-dimensional fitting, and the fitting in the second way is a three-dimensional fitting. In other embodiments, the fittings in both ways are three-dimensional fittings.

In addition to setting the bed position, the fit patient model may be used to set scan parameters of the medical system.

In further embodiments, a medical professional is signaled, such as signaling completion of the fitting in the first way, the fitting in the second way, results of the monitoring, and/or the adjusting of the bed position.

In a second aspect, a medical system includes a depth sensor configured to measure over a sequence. The medical system includes an image processor configured to detect a patient on a bed from measurements of a first part of the sequence, to determine landmark locations of the patient from measurements of a second part of the sequence, and to fit a patient model to measurements of a third part of the sequence. The bed is configured to be moved based on the fit of the patient model.

In one embodiment, the image processor is configured to monitor motion of the patient on the bed in response to the detection and to fit in response to a lack of motion and based on the landmark locations. In another embodiment, the image processor is configured to fit the patient model to measurements of a fourth part of the sequence, wherein the bed is configured to be moved from a location based on the fit of the patient model using the third part to a location based on the fit of the patient model using the fourth part. In yet another embodiment, the image processor is configured to fit the patient model as initialized by the landmark locations.

In a third aspect, a method is provided for patient model estimation from surface data in a medical system. A three-dimensional camera captures a stream of the surface data representing an outer surface of a patient at different times. The patient is monitored for movement using the stream. The patient model is fit using the surface data from the different times. A first of the times occurs before or during a period where the movement of the patient is below a first threshold, and a second of the times occurs after triggering due to the period exceeding a second threshold. The medical system is configured based, at least in part, on the patient model as fit.

In a further embodiment, the fitting using the surface data of the first of the times includes detecting landmark locations, and the fitting using the surface data of the second of the times includes fitting a three-dimensional mesh to the surface data of the second of the times and based on the detected landmark locations.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

FIGS. 4 and 5 are flow chart diagrams of other embodiments of methods for patient model estimation from surface data in medical systems;

FIG. 6 illustrates a fitting process based on stream capture;

DETAILED DESCRIPTION OF EMBODIMENTS

Patient model estimation is from a three-dimensional camera stream. Automatic patient positioning is extended by acquiring RGBD images of the patient as a live stream (e.g., a sequence of RGBD images) during the scan workflow. The stream is analyzed multiple times (e.g., continuously or periodically) to detect different patient poses or changes in pose. The radiographer need not explicitly acquire a snapshot before positioning the patient for scan as the stream is analyzed.

In one embodiment, the workflow for automatic patient positioned is extended to include table occupancy detection and/or and change detection stages for efficient handling of stream data before proceeding to following stages. The table occupancy detection stage detects if the table is occupied by the patient and accordingly notifies to system to proceed to the body change detection stage. The change detection stage may include image-based and/or landmark-based methods to detect change or movement of the patient in the images. The more computationally complex avatar fitting stage occurs when there is no patient movement detected in the stream. If a fit avatar from earlier frame is available, the system performs the fine avatar fitting initialized by the earlier fit altered to accommodate the change in the patient pose.

Figure 1:
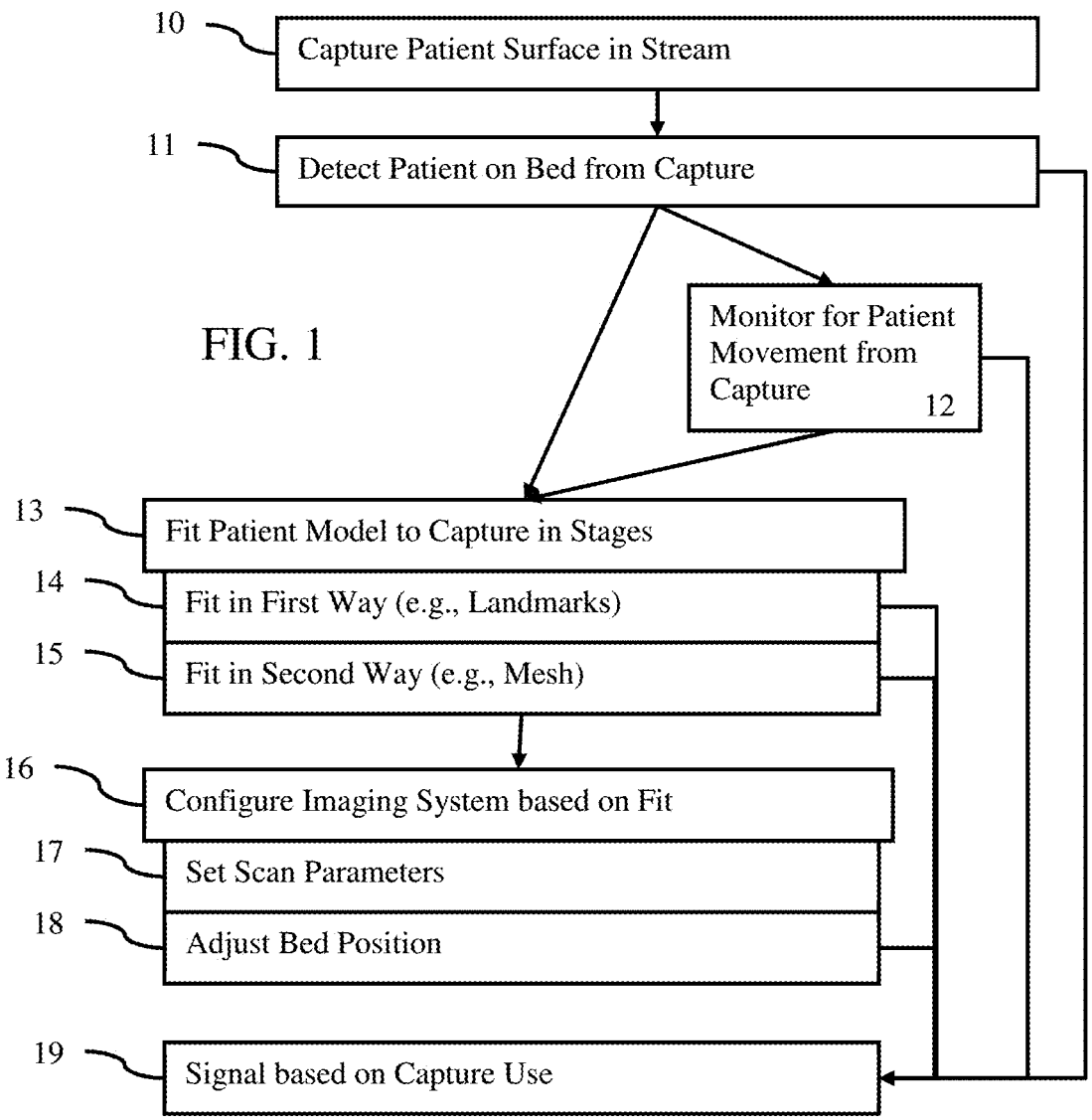
FIG. 1 is a flow chart diagram of one embodiment of a method for patient model estimation from surface data in a medical system.

FIG. 1 is a flow chart diagram of one embodiment of a method for patient model estimation from surface data in a medical system. Streaming or a sequence of image captures is integrated into a workflow for patient treatment or imaging. Different parts of the patient fitting are performed at different times to assist in automated or semi-automatic fitting of the patient model. The stream may be used to update, such as monitoring the patient and updating when the patient moves. The current fit patient model is used to configure the medical system for the patient.

Figure 3:
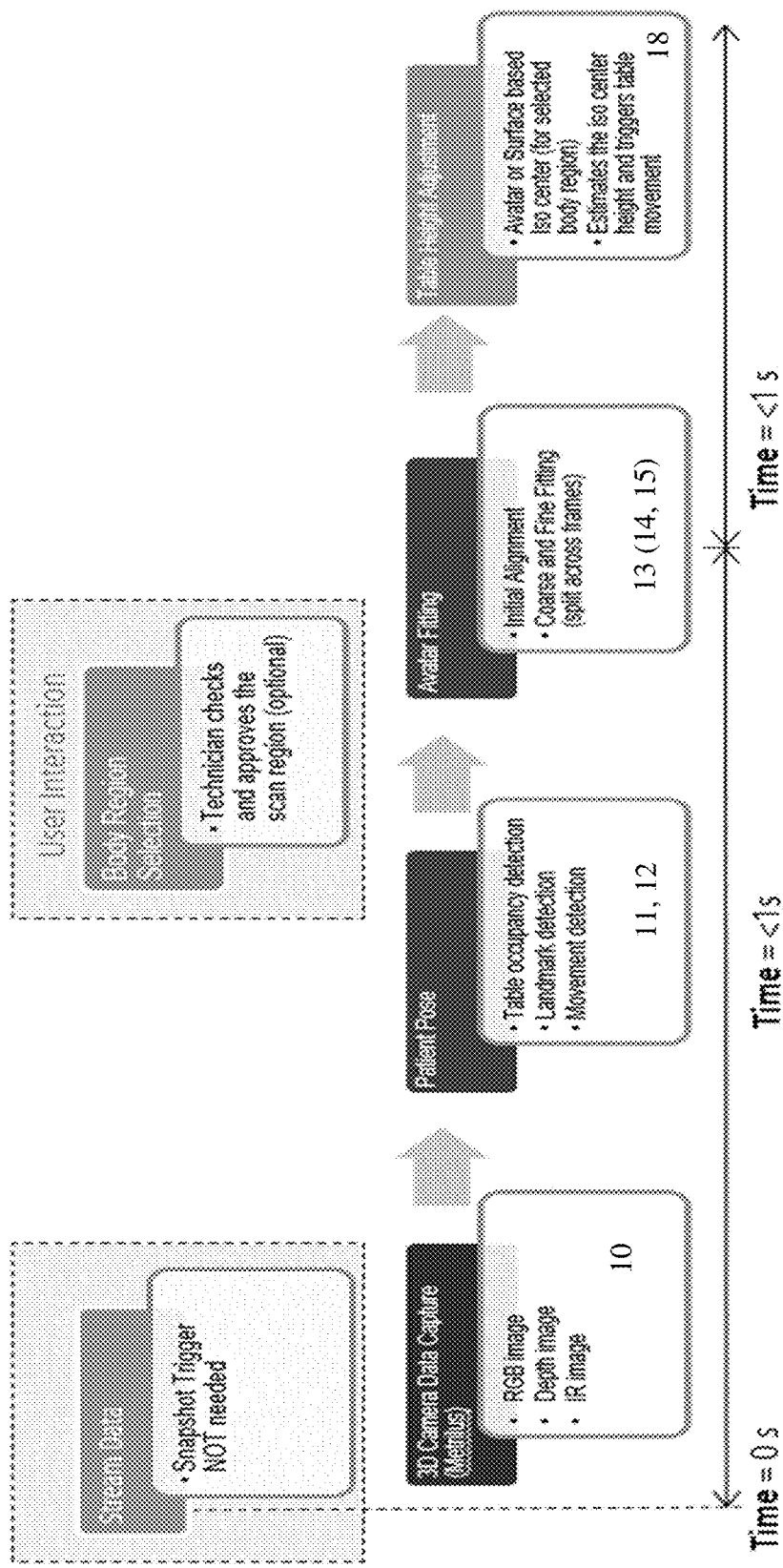
FIG. 3 illustrates one embodiment of patient model estimation using streaming.

FIGS. 3-5 show other example embodiments of the method of FIG. 1. FIG. 3 shows relative timing for different uses of the stream. FIG. 4 shows an embodiment where landmarks are initially fit in two dimensions and the mesh is then fit in three dimensions. FIG. 5 shows an embodiment where the landmarks and mesh are fit in three dimensions. In the discussion below, FIGS. 3-5 are discussed in conjunction with FIG. 1.

Figure 8:
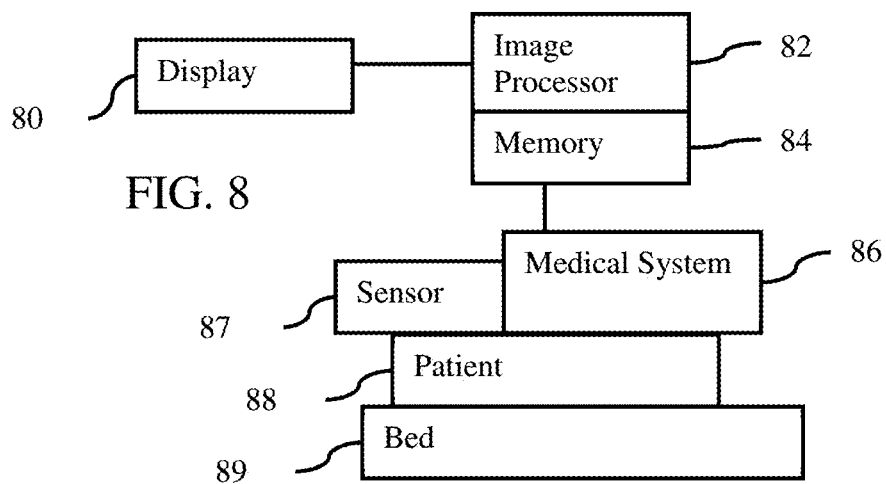
FIG. 8 is a block diagram of one embodiment of a medical system using patient model estimation.

The method of FIG. 1 is performed by a medical system, such as the medical system of FIG. 8. The medical system may be a medical imaging system (e.g., CT scanner, magnetic resonance (MR) scanner, positron emission tomography (PET) scanner, single photon emission computed tomography (SPECT) scanner, ultrasound scanner, x-ray scanner, or other diagnostic imaging scanner) and/or a medical therapy system (e.g., x-ray therapy system). A depth camera captures the patient surface. An image processor fits the model, monitors the stream for patient detection and/or motion. The image processor or another controller may configure the medical system based on the fit. The image processor or another controller may signal the user based on the fit, detection, or monitoring. Other devices may be used to perform any of the acts.

The method is performed in the order shown (e.g., top to bottom or numerical), but other orders may be used. For example, act 14 is performed prior to act 12 and/or during act 12. As another example, act 12 may be performed at any time after act 11. In another example, act 19 is performed during or immediately after any of acts 12-18.

Additional, different or fewer acts may be provided. For example, act 19 is not provided. As another example, acts 17 and/or 18 are not provided. In other examples, acts 11 and/or 12 are not used.

In act 10, a sensor captures an outer surface of a patient. The sensor is a depth sensor or three-dimensional camera, such as a 2.5D or RGBD sensor (e.g., Microsoft Kinect 2 or ASUS Xtion Pro). The depth sensor may directly measure depths, such as using time-of-flight, interferometry, or coded aperture. The depth sensor may be a camera or cameras capturing a grid projected onto the patient. The sensor or three-dimensional camera may be multiple cameras capturing 2D images from different directions, allowing reconstruction of the outer surface from multiple images without transmission of structured light. Other optical or non-ionizing sensors may be used.

The sensor is directed at a patient. The sensor captures the outer surface of the patient from one or more perspectives. Any portion of the outer surface may be captured, such as the entire patient viewed from one side from head to toe and hand to hand or just the torso. The sensor captures the outer surface with the patient in a particular position, such as capturing a front facing surface as the patient lies in a bed or on a table for treatment or imaging.

The outer surface is the skin of the patient. In other embodiments, the outer surface includes clothing. The sensor may use a frequency that passes through clothing and detects skin surface. Alternatively, the outer surface is the clothing and the fitting of the patient model accounts for the clothing.

Figure 2:
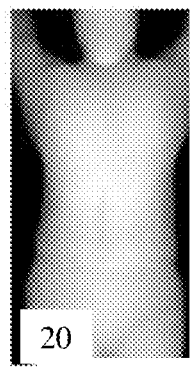
FIG. 2 is an example depth image.

The outer surface is captured as depths from the sensor to different locations on the patient, an image or photograph of the outside of the patient, or both. The sensor outputs the sensed image and/or depths. The measurements of the outer surface from the sensor are surface data for the patient. FIG. 2 shows an example image 20 from surface data where the intensity in grayscale is mapped to the sensed depth. Alternatively, the sensor measurements are processed to determine the outer surface information, such as stereoscopically determining the outer surface from camera images from different angles with image processing.

In one embodiment, the surface data may include different representations of the patient. Two or more channels are created. For example, two images have pixel intensity modulated by the amplitude of the information for the channel (e.g., one by depth and the other by color). In one embodiment, given a 3D surface of the patient's body (skin surface), 2D projections of this data—skin surface image (e.g., height of the surface from the scanner table at each location in the image) and depth image (e.g., measure the thickness of the person at each location in the image)—are formed by image processing from the output of the sensor. Each channel provides different information. One channel provides a distance or height of front surface locations to a bed or table on which the patient lies, to the sensor, and/or relative to another location. The outer surface as sensed and the known location of the sensor to the bed are used to determine the distance. Another channel is a thickness of the patient. The thickness may be a difference of a given depth from the maximum and minimum depth. Other thickness may be used. The first channel stores the depth of the body surface as observed from the front or looking at the patient resting on the patient bed, and second channel stores the thickness computed by measuring the distance between the closest and furthest point as observed from the front. Other channels may be used, such as one channel for depth from the sensor and another channel for optical image of the patient. Other surface data may be used.

The surface data is used at the resolution of the sensor. For example, the surface data is at 256×256 pixels. Other sizes may be used, including rectangular fields of view.

The capture is of a stream. Frames of surface data representing the patient at different times are acquired in a sequence. The stream may be constant, such as capturing frames at any rate (e.g., 20 Hz). Periodic capture may be used, such as every second. The frequency may vary over time. In alternative embodiments, the sequence is captured using triggering. In response to each of multiple triggers or triggering events, one or more frames of surface data are captured.

The stream provides depth camera measurements (e.g., surface data) in a temporal set of frames. Since the surface data represents three dimensions, a 3D+t stream of point cloud data is provided.

The surface data may be filtered and/or processed, such as provided in act 40 of FIGS. 4 and 5. For example, the surface data is altered to a given resolution. As another example, the surface data is down sampled, such as reducing 256×256 to 64×64 pixels. Each pixel may represent any area, such as each pixel as down sampled to 64×64 representing 1 cm$^2$ or greater. Alternatively, the sensor captures at this lower resolution. The surface data may be cropped, such as limiting the field of view. Both cropping and down sampling may be used together, such as to create 64×64 channel data from 256×312 or other input channel data. Greater or lower resolution may assist in regression.

In another approach for act 40, the surface data is normalized. The surface data is rescaled, resized, warped, or shifted (e.g., interpolation). The surface data may be filtered, such as low pass filtered. The normalization may use reprojection to provide the surface data from a common or preset view direction and distance.

In act 11, the image processor detects the patient on the bed from the surface data of the stream. The bed is a table or platform upon which the patient rests or is placed for imaging or therapy. In the CT scanner example, the patient lays on the bed. The bed may then move the patient into the scanning chamber (i.e., moves the patient along a center axis of a cylinder housing the gantry of the CT scanner).

The camera may capture surface data from before the patient is placed on the bed, such as starting to capture upon power-up, triggered by the user, or triggered by an appointment in a schedule. Since a stream is captured, a sequence of frames of surface data representing the bed without and with the patient is acquired. Once the patient is placed or starts to lay upon the bed, the surface data reflects the patient on the bed. The table (bed) occupancy detection stage detects if the table is occupied by the patient and accordingly notifies to system to proceed to a body detection stage. The detection of the patient may or may not continue once the patient is detected.

The image processor uses the surface data to detect that the bed is occupied. The surface data is image processed. In one embodiment, difference images are formed from the surface data where one image is of the bed known to be without a patient. When the average difference in color and/or depth is above a threshold, then the patient is detected. In another embodiment, template matching is performed. A template of a frame of surface data with an average sized patient laying on the bed is compared to each frame of surface data captured. Once the match (e.g., correlation) with the template is above a threshold, the patient is detected. Other image processing may be used.

In one embodiment, the image processor detects the patient from the surface data by input of the surface data or a value or values derived from the surface data (e.g., gradients) into a machine-learned model, such as a neural network. The machine-learned model is any machine-learned classifier outputting a detection. A fully connected neural network, convolutional neural network, or another neural network may be used. A support vector machine, clustering based machine learning, Bayesian, or other machine-learned model may be used.

For training the machine-learned model, the machine learning model arrangement or architecture is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning. Training data, including many samples of frames of surface data and the corresponding ground truth (i.e., patient or no patient), is used to train. The relationship of the input surface data to the output patient or no patient is machine learned. Once trained, the machine-learned model may be applied to detect the patient on the bed.

The training and application may be used for any of the machine-learned models for detection, monitoring, and/or fitting. Different machine-learned models are trained and applied for different purposes.

In act 12, the image processor monitors the patient for movement. Once the patient is detected, the capture of the stream continues. The frequency of capture may be increased for monitoring as compared to detecting. This monitoring is available due to the availability of the stream or sequence of captures of the surface data.

The monitoring of patient motion is performed in order to determine when the patient is motionless enough that the bed and patient may be positioned for scanning and/or scan settings may be determined. Once the patient is generally motionless, the patient is ready to be imaged or treated. More computationally complex operations for fitting of the patient model to the surface data for a current patient may be reserved until after the patient is generally motionless.

The image processor monitors for change in patient position. The surface data is monitored to show the change. In one embodiment, difference images are generated from the color and/or depth measurements. The most recent pair of images are compared, such as a minimum sum of absolute differences, average difference, or correlation. Where the comparison shows similarity below a threshold (i.e., dissimilar), the patient is moving or changing position. In another embodiment, a machine-learned model is used. The machine-learned model was trained to detect movement in response to input of frames of surface data from different times. A long term-short term or other temporal-based architecture and corresponding machine-learned model may be used. In yet another embodiment, landmark detection is used. Image processing or a machine-learned model(s) is used to detect one or more landmarks. The position or positions of the landmarks at different times are compared. Where the positions are within a threshold difference, there is no movement.

The movement of the patient is detected as a change in patient position using the stream. The state and motions of the patient are detected from the temporal 3D+t point cloud data. The change in images of the surface data (e.g., change in color or depth) indicates movement of the patient from one frame to another frame.

To identify when the patient is stable (i.e., not moving or ready to image or treat), the monitoring continues. A lack of motion over a period is desired. For example, no motion over five, ten, thirty, sixty or other number of seconds is desired. The threshold period may be any number of seconds and/or any number (e.g., one, two, three or more) number of minutes. The amount or length of time over which movement is below a threshold amount is compared to a period threshold.

The patient model is to be fit to the patient. Different parts of this fitting occur at different times based on the monitoring. For example, the monitoring itself may be part of the patient model fitting. By detecting the location of landmarks, a patient model including landmarks may be partially fit to the surface data for the patient. The detection of lack of movement over a given period may trigger computation or further fitting of the patient model. The computationally complex part of the fitting is performed after the patient is steady, conserving computation resources. If the patient is later detected to move, the fine fitting or coarse and fine fitting may be repeated. The monitoring of act 12 is used to provide part and/or separate the fitting. The stream of captured surface data allows for this separation.

As shown in FIG. 3, an initial patient pose is determined by detecting table occupancy by the patient in act 11 and monitoring movement of the patient in act 12, such as by landmark detection. This initial patient pose is an initial or coarse fit of the patient model to the surface data captured in act 10. These operations may be performed in less than one second, so are repeated in continuous or regular monitoring. Once the initial or coarse pose is stable, further fitting is performed in act 13. This further fitting of act 13 is split across two or more frames of the surface data and each part may take less than 1 second.

The detection of the patient may activate the fitting of act 13. The detection activates the monitoring of act 12. Where the monitoring uses landmarks, other coarse fitting, or other pose determination, the patient model is at least partially fit to the surface data.

In act 13, the image processor fits the patient model using the surface data from different times. For example, surface data from a time or period before or during the patient movement being below a threshold and from another time or period after the period of no or little movement reaches a threshold is used. As another example, one or more frames prior to the monitoring showing no movement over a threshold length of time are used for coarse fitting, and one or more frames during no or little movement and after a threshold length of time of no or little movement is reached are used for fine fitting. Reaching the threshold period of no or little movement triggers the more complex fine fitting. The computationally intensive avatar fitting is split into multiple steps so that the system is responsive and does not delay in computing the latest patient pose for each image processed.

FIG. 6 shows an example of this separation. After capture and then shape initialization (e.g., occupancy detection and identifying landmarks) in act 60, an initial alignment 61 is performed, such as detecting landmarks represented in the surface data for the patient and positioning landmarks of the patient model at the three-dimensional locations of the detected landmarks. This is an initial fitting of the patient model to align the surface cloud to the avatar template (patient model). In a further fitting, another or the same frame of surface data is used for a coarse fitting. A shape, such as outer surface represented by a mesh, of the patient model is fit to or changed to correspond with detected landmarks from the surface data in act 14. The relative position of the landmarks are used to warp the surface mesh. A detailed or fine fitting aligns the surface mesh of the patient model to the surface data in act 15. This detailed shape fitting uses one or more later frames of surface data once the patient is ready to treat or image. An iterative registration, fitting, and/or shape projection (e.g., projection of shape from the view direction of the camera to match the fit patient model to the surface data measurements) are performed, such as using an iterative matching or optimization. Where time is of the essence, such as for a trauma case, this fitting may not be performed. In act 62, the fit is verified. The patient model as fit is checked against expected or possible pose, such as assuring that angles and/or distances of parts of the body to each other are within expected ranges.

In FIG. 1, these different stages of fitting are provided by acts 14 and 15. Each stage represents a different way of fitting, such as coarse and fine, landmark and mesh, and/or other differences in approach to fitting a patient model to data representing the patient (surface data). Additional fitting stages may be provided, such as three or more different ways represented by different stages or types of fitting of the patient model to the surface data (e.g., coarse, medium, and fine fitting).

The patient model is a generic representation of a surface of a human or part of a human. Different models may be used for different body types, such as a male or female model. The patient model is not specific to the patient. For example, the patient model is a statistical shape model. The patient model is not specific to any other patient or is specific to a patient meeting a norm.

Any representation may be used for the model. In one embodiment, the model is formed from a mesh, such as a mesh of triangles. Other meshes may be used. Other representations of a 3D surface may be used.

The image processor fits the patient model to the surface data for the patient to be treated or imaged. The fit transforms or distorts the patient model based on the sensed outer surface of the patient. The generic patient model is personalized to the outer surface of the patient by fitting to the surface data. The fit may be an iterative optimization, such as testing different alterations of the model where the alteration is controlled based on a closeness of fit or difference between the model and the surface data.

Any now known or later developed fit of a body surface model to captured surface data for a patient may be used. For example, a shape completion and animation of people (SCAPE) model is fit to the surface data based on minimization of differences. In one embodiment, the depth camera image 20 of a subject is converted to a 3D point cloud. A plurality of anatomical landmarks is detected in the 3D point cloud. A 3D avatar mesh is initialized in act 14 by aligning a template mesh to the 3D point cloud based on the detected anatomical landmarks. A personalized 3D avatar mesh of the subject is generated by optimizing the 3D avatar mesh in act 15 using a trained parametric deformable model (PDM). The optimization is subject to constraints that take into account clothing worn by the subject and the presence of a table on which the subject is lying.

In another embodiment, a statistical shape model is fit to the depths as the surface data. The statistical shape model is a mesh or other representation of an average or other statistical representation of an outside of a human or part of a human. The statistical shape model includes probabilities or other constraints on alteration, so that the fitting maintains the shape based on statistics.

In yet another embodiment, a personalized 3D mesh of a person is generated by a model-based approach to fit a human skeleton model to depth image data of the person in act 14. The estimated pose skeleton is then used to initialize a detailed parametrized deformable mesh (PDM) that was learned in an offline training phase. The PDM is then optimized in act 15 to fit the input depth data by perturbing the body pose and shape. A sampling-based optimization procedure fits the PDM to the depth data. Unlike the SCAPE model, which is only applied to data with a skin clad subject, the sampling-based approach deals with clothing variations of the subject. Furthermore, the sampling-based approach also enables embodiments to deal with bias introduced due to sensor noise.

FIGS. 4 and 5 show the fitting in different stages and corresponding ways. After capture of RGBD surface data in act 10 and any preprocessing of act 40 (e.g., normalization and reprojection to a given view from a given distance, and/or surface normal computation), the patient is detected in act 11. The detection is based on the surface profile and/or a machine-learned detector. If the patient is not detected, the process returns to capture the next frame in act 10.

If the patient is detected, an initial fit is performed in act 14. Landmarks (e.g., neck, navel, joints, and/or other body surface landmarks) are detected using one or more machine-learned models, such as fully connected networks. This fitting of the patient model to landmarks provides fitting in one way. The fitting of the patient model in this first way is activated upon detection of the patient and may be repeated using other frames of surface data until monitoring in act 12 shows no motion for a given period. In this way, the model landmarks are fit to the landmarks detected from the surface data at one or more times. A plurality of temporally consistent anatomical landmarks in the 3D+t point cloud data are detected and used in a coarse or initial fitting. In a further embodiment, the placement of one or more internal landmarks are estimated (e.g., using a machine-learned model) from the surface data and used in the fitting of the patient model. A plurality of surface and/or internal body landmarks that are regressed from the subject's appearance in the 3D point cloud at each time instance are used for fitting the patient model.

In other embodiments, the initial or coarse fit using landmarks is performed after consistent and stable detection of little or no movement of the patient in a time window T. In a subsequent frame of surface data, a plurality of anatomical landmarks and orientations are regressed from the 3D point cloud using a respective trained regressor.

In FIG. 4, the position of the landmarks is detected in two dimensions. A two-dimensional fitting is performed based on two-dimensional landmark regression. In FIG. 5, the position of the landmarks is detected in three dimensions. A three-dimensional fitting is performed based on three-dimensional landmark regression.

In act 12, patient motion or position change is monitored. If the patient changes position within a threshold period, the process returns to capturing in act 10 for further monitoring 12 with or without repetition of fitting in act 14. Due to detected motion, the initial or coarse fit of act 14 may be repeated.

Once the motion is stable for sufficient time, further fitting or fitting in a different way is performed in act 15 using a subsequent frame of surface data. In the embodiment of FIG. 4, the two-dimensional landmark locations are found in three dimensions in act 42. A local extrema search in the surface data and/or a machine-learned detector of a local peak are used to locate the landmarks in three dimensions.

In act 15, the image processor fits the previously partially, initially, or fully fit patient model to the surface data. The fitting is in a different way, such as using a different machine-learned classifier, a different process, different landmarks, different cost function or fit measure, different optimization, and/or another difference in fitting. In one embodiment, the earlier fitting included fit based on landmarks. This further or refined fitting fits a surface mesh of the patient model based on the surface represented by the surface data. The landmarks provide an initial fit (e.g., pose or position and orientation) that is refined by fitting the surfaces.

The results from the previous fitting are used. For example, the landmarks provide an initial fitting. The mesh of the patient model is placed and/or warped based on the locations of the landmarks. As a result, the mesh is more likely initially closer to the actual surface of the patient represented in the surface data. As another example, the fitting using an earlier frame of surface data indicates a pose of the patient, providing a translation and/or orientation fit. The further fit then warps the surface. In yet another example, an earlier fitting provides a warped surface. Due to change in position (e.g., booster or rest added for patient comfort), the fitting is performed again using the earlier fit as a starting point without or with consideration for a region or regions being detected as associated with change in position. As yet another example, locations of landmarks from an earlier fitting are used to limit a search space, such as a search for other landmarks used in a refined fitting.

In one embodiment, the image processor generates a personalized three-dimensional avatar mesh of the subject by refinement of the initial mesh on the three-dimensional surface data. The three-dimensional avatar mesh is initialized on a selected 3D point cloud data of a selected time. If the avatar from earlier frame is available, the system performs the fine fitting to accommodate the change in the patient pose.

Any of the stages of fitting may use constraints. For example, the patient model may include limitations on relative angles and/or positions of different parts. There may be constraints for the bed position and/or constraints for non-patient objects. The bed, non-patient objects (e.g., clothing, bolsters, supports, patient comfort devices, instruments, and/or user interface devices), and/or environmental factors may be detected or have known locations and are used to constrain the fitting as the patient cannot occupy the same space as the bed and/or non-patient objects. The generation and/or updating of the three-dimensional avatar mesh for each temporal instance may incorporate constraints derived from a plurality of sources including but not limited to table location, velocity of the bed, acceleration of the bed, and forces applied by the bed. As the bed moves to place the patient for treatment and/or imaging, the monitoring of act 12, accounting for bed motion, may continue. The patient model may be updated, such as updating the translation position of the patient model relative to the medical system. The patient model may be updated to account for distortions or changes in the surface of the patient and/or in internal organ position due to the acceleration or forces caused by movement.

The fit patient model indicates the position of the patient relative to the bed and/or medical system. The patient model may include internal organs or landmarks that are positioned according to regression or relationship from the fit surface mesh and/or external landmarks. The patient model as fit indicates a center line for the patient and/or a location in one, two, or three dimensions of a region of interest on or in the patient.

In act 16, the medical system is configured, at least in part, based on the patient model as fit to the patient. The image processor or a controller of the medical system sets one or more values of programmable variables for imaging or treating the patient. The medical scanner may configure itself. The image processor may provide information to a controller of the medical scanner to configure. The image processor may configure by direct control of the medical scanner. Alternatively, the user manually configures the medical scanner based on the fit model by entry with one or more user inputs. The configured medical system may then treat or image the patient using the values.

FIG. 1 shows two possible configuration considerations, configuring the bed position in act 18 and configuring scan parameters in act 17. Other configuration parameters may be used.

In act 17, one or more scan parameters are set. After consistent and stable detection of the three-dimensional avatar mesh in a time window T, additional scan parameters are computed. The scan parameters may be a region of interest or range. For example, the fit patient model indicates the locations of start and end points for a range of scanning along a torso of the patient. Based on the reason for the scan (e.g., region to diagnose and/or to treat), the fit patient model is used to control the movement of the gantry or range of scanning. The intensity used (e.g., dose) may be set, such as based on a size of the patient determined from the fit model. The patient model as fit may define a field of view and/or x-ray intensity to control dose or scan range. The fit model may be used to select scan sequence, coil placement, and/or scan position for magnetic resonance (MR) scanning. For fluoroscopy using dyna-CT scans, the fit model may be useful for positioning the scanner and controlling the x-ray source. Any setting or parameter of the medical scanner may be determined or configured based on the fit model or a value (e.g., estimated weight or height) derived from the fit model. The pose, scan range and/or iso-center of the scan range may be based on the fit model.

In act 18, the bed position is adjusted. The bed may move along one or more dimensions. For example, the bed is moveable using robotics or an adjustable-motorized base along three dimensions (i.e., along a bore of the medical system, up and down, and left and right). The patient may not be centered on the bed and, even centered, different patients have different centers due to size. The fit patient model indicates the location of the patient and/or any region of interest in or on the patient. For example, the part of the patient to be treated and/or imaged is centered at an iso-center of the medical system. The bed moves the patient to provide this positioning. The patient model, as fit, indicates the location on or in the patient. In another example, the bed is positioned at different locations at different times during treatment or scanning. The fit model is used to control or establish the proper positioning. As another example, a center of the patient determined from the patient model fit to the patient is moved to an iso-center of the medical system.

The configured medical scanner scans the patient. The patient is treated or imaged based on the settings and/or bed position. The imaging or treatment is performed based on the configuration of the medical scanner. For therapy, the therapeutic system may apply a radiation dose based on the configuration from the patient model as fit.

The monitoring of act 12 may continue after completion of fitting in act 13 (e.g., after a coarse fitting in act 14 and a fine fitting in act 15 to the surface data from one or more times). The fitting of acts 13, 14, and/or 15 is repeated using surface data from another time. For example, the patient position is changed, such as due to comfort, rotating for further treatment or imaging, or other reason. This variation in the patient position triggers refitting. The workflow may proceed to the beginning, such as starting from act 12. The three-dimensional avatar mesh is updated at each temporal instance of the point cloud after any detected change in position. The bed position and/or other configuration of the medical system is then updated based on a new fit patient model.

In one embodiment, the fine fitting is repeated to update. The previous fit is used as a constraint, such as to define a search area for fitting. Where the change in position is isolated to a particular region (e.g., arm), the fitting may be constrained to that region of interest. The region of interest may be used to limit or constrain fitting in other ways. For example, fine-grained movement and state analysis is restricted to the region of interest based on the body region to be scanned. Just the part of the patient model associated with the region of interest is refined or updated. Alternatively, the whole patient model is refined or updated.

In act 19, the image processor signals a medical professional. The signaling is audible and/or visual. The signaling may be a warning, recommendation, and/or informative.

The signaling may occur for any of various reasons or triggers. For example, completion of the fitting in the first way, completion of the fitting in the second way, results of the monitoring (i.e., motion or no motion), and/or the adjusting of the bed position are signaled. In one embodiment, the professional and/or patient are warned that the bed is going to move. In another embodiment, the signaling is for the patient to hold still and is provided based on detected motion during monitoring. The signaling may indicate one or more values of settings or configuration information, such as to allow the radiographer to confirm proper or desired settings. If any configuration is to be updated or is updated, the signaling may indicate this change in status.

The streaming capture of depth and/or color as the surface data or images may allow for more automation in the workflow. For example, the bed position is adjusted without the user having to manually indicate where the bed is to be located and/or manually to cause the bed to move. Instead, the fit patient model is used to move and position the bed. The user may confirm activation of the move, but the movement and/or position to which the bed is moving are controlled automatically. The fitting occurs automatically without any user input relative to any of the camera images or surface data. In one embodiment, the user activates the workflow for a particular use for a patient. In response, the streaming starts. The medical professional may assist the patient onto the bed and make the patient comfortable. The streaming capture is used to detect occupancy, monitor movement, and fit the patient model in different stages. The medical professional does not need to activate or control the detection, monitoring, or fitting. The bed position and/or some settings are configured based on the patient model without medical professional input. A request for confirmation may be provided. The medical professional may alter a setting or input other settings.

Figure 7:
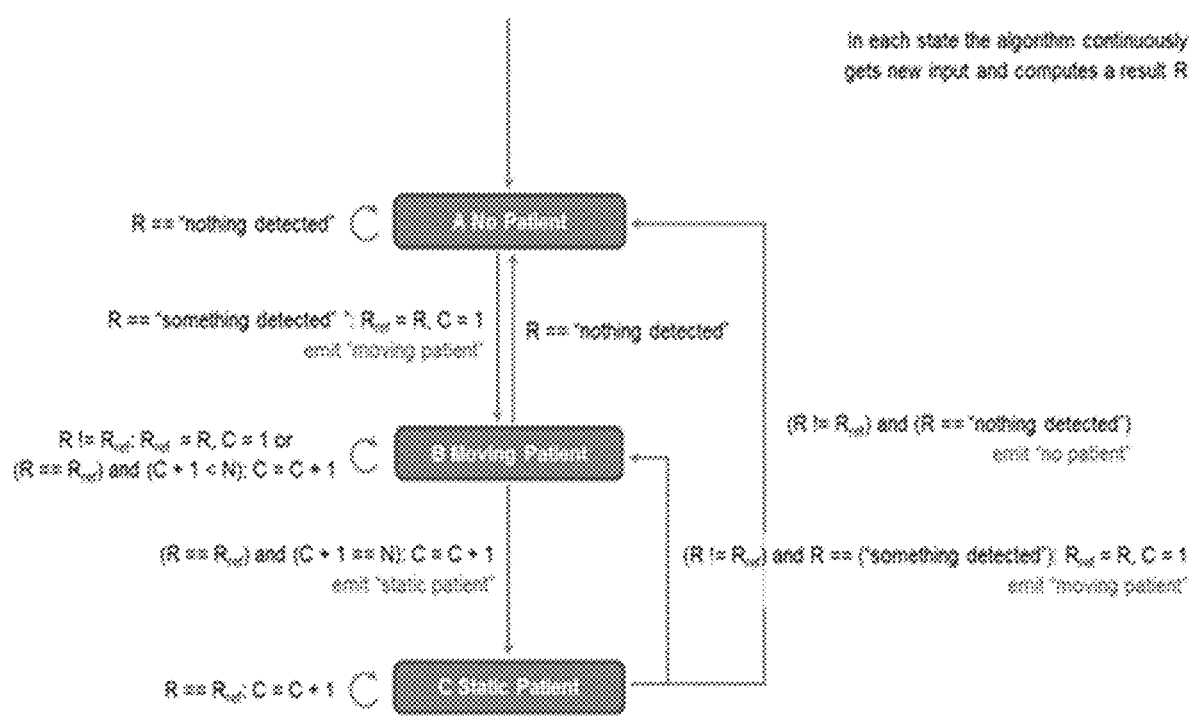
FIG. 7 is a state diagram using depth camera streaming for patient modeling.

FIG. 7 illustrates the separation of actions in fitting and configuration provided by streaming capture. Three states relative to the patient are shown as A—no patient, B—moving patient, and C—static patient. In state A, the result R is either nothing detected or something detected. If the result is patient detection, then the state transitions to B. In state B, the moving patient is monitored with the results being nothing detected due to movement off the bed, the patient continuing to move, or the patient as static. If the patient is not detected, the state transitions back to A. If the patient is moving, the state remains in B. If the patient is static, the state transitions to C. In state C, the results are remaining static, transitioning to A where no patient is detected, or transitioning to B when the patient moves.

In the transition from A to B, a reference frame of surface data (e.g., image) is defined. This reference is used to detect movement initially. In state B, the reference is updated as each new frame is captured, such as using the most recent past frame of surface data as the new reference. In the transition from B to C, the frame of surface data most recently used to establish static patient is used as a reference for monitoring that the movement continues to be static.

The same or different frames are used for fitting. The patient states and movement are detected in a cascaded framework. The fitting cascades from coarse-to-fine grained. Each granularity affects one or more scan parameters and radiographer signaling mechanisms.

FIG. 8 shows one embodiment of a medical system using a sequence of sensor captures for patient model fitting. The medical system includes the display 80, memory 84, and image processor 82. The display 80, image processor 82, and memory 84 may be part of the medical system 86, a computer, server, workstation, or other system for diagnosis or treatment. A workstation or computer without the medical system 86 may be used as the medical system. The medical system also includes the sensor 87 for sensing (imaging) an outer surface of a patient.

Additional, different, or fewer components may be provided. For example, a computer network is included for remote image generation of locally captured surface data or for local fitting from remotely captured surface data. The fitting is applied as a standalone application on the workstation or a local device or as a service deployed on network (cloud) architecture. As another example, a user input device (e.g., keyboard, buttons, sliders, dials, trackball, mouse, or other device) is provided for user alteration or setting for configuring the medical system 86. In yet another example, the medical system 86 is not provided.

The sensor 87 is a depth sensor or camera. LIDAR, 2.5D, RGBD, stereoscopic optical sensor, or other depth sensor may be used. One sensor 87 is shown, but multiple sensors may be used. A light projector may be provided. The sensor 87 may directly measure depth from the sensor 87 to the patient. The sensor 87 may include a separate processor for determining depth measurements from images, or the image processor 82 determines the depth measurements from images captured by the sensor 87. The depth may be relative to the sensor 87 and/or a bed or table 89.

The sensor 87 is directed to the patient 88. The sensor 87 may be part of or connected to the medical therapy system 86 or is separate from the medical system 86.

The sensor 87 is configured to measure depths to or for a patient. The depths are distances from the sensor 87, table 89, or other location to the patient at various locations on the patient. Any sample pattern over the patient may be used. The sensor 87 outputs depth measurements and/or a surface image as one frame of data for an entire field of view.

The sensor 87 measures over a sequence. The depths and/or images (e.g., RGBD) are measured at a given time. This is repeated at different times, providing frames of surface data representing the patient at different times.

The image processor 82 is a control processor, general processor, digital signal processor, three-dimensional data processor, graphics processing unit, application specific integrated circuit, field programmable gate array, artificial intelligence processor, digital circuit, analog circuit, combinations thereof, or other now known or later developed device for processing surface data. The image processor 82 is a single device, a plurality of devices, or a network. For more than one device, parallel or sequential division of processing may be used. Different devices making up the image processor 82 may perform different functions, such as fitting a mesh as a patient model by one device and estimating weight by another device. In one embodiment, the image processor 82 is a control processor or other processor of a medical therapy system 86. The image processor 82 operates pursuant to and is configured by stored instructions, hardware, and/or firmware to perform various acts described herein.

The image processor 82 is configured to detect a patient on the bed 89 from measurements of the sensor 87. The measurements from one part of the captured sequence, such as a current frame or the earliest frames in an ongoing capture, are used. These measurements are processed to detect occupancy of the bed 89. Patient detection allows the image processor to trigger fitting of the patient model and monitoring for patient motion.

The image processor 82 is configured to fit a patient model to the surface data. A frame or multiple frames of measurements from the sensor 87 are used to fit the patient model. The frame or frames are from a different part of the sequence, such as being a frame or frames captured after the frame or frames for which occupancy is initially detected.

The fitting may be an initial, partial, or coarse fitting. For example, a rigid fitting is provided before a non-rigid fitting. As another example, a coarse fitting is provided before a fine fitting. In one embodiment, the image processor 82 determines landmark locations of the patient from the measurements. Any number of landmarks may be detected and located.

The image processor 82 is configured to fit the patient model to measurements of yet another part of the sequence. For example, after fitting using landmarks and once monitoring shows no or little patient motion, measurements from one or more subsequent frames associated with no or little movement are used to fit the patient model. A mesh or three-dimensional surface is fit to the measurements. The fitting may be initialized by the landmark locations or previous fitting. The previous fitting may be used to center and/or limit the search space for the fine or surface fitting.

The image processor 82 may be configured to perform further fitting using other parts of the sequence of captured measurements. For example, the patient 88 moves after the patient model is fit. The image processor 82 refits using current frames.

The image processor 82 is configured to monitor motion of the patient on the bed 89. The monitoring begins in response to the detection of occupancy. The fitting may occur based on the monitoring. For example, a coarse fit (e.g., matching landmarks) is repeated until the patient is static. Once there is a lack of motion, a fine fitting (e.g., matching surfaces) is performed. This fine fitting may be based on landmark locations, such as initializing the initial warping and/or location of the surface of the patient model based on the matching of the landmark locations.

The image processor 82 is configured to form a mesh for the patient using the depths from the sensor 87. A mesh is fit to the depths or other output of the sensor as a patient model. The mesh may be fit by detection of the surface of the patient and/or by minimizing differences between a pre-determined mesh shape and the shape represented by the output of the sensor.

The display 80 is a CRT, LCD, projector, plasma, printer, tablet, smart phone or other now known or later developed display device for displaying the output. The display 80 is configured by loading an image into a buffer. The display 80 is configured to display an image of the patient from the sensor 87 or signaling.

The sensor measurements, fit shape model, surface data, machine-learned model, occupancy, motion state, and/or other information are stored in a non-transitory computer readable memory, such as the memory 84. The memory 84 is an external storage device, RAM, ROM, database, and/or a local memory (e.g., solid state drive or hard drive). The same or different non-transitory computer readable media may be used for the instructions and other data. The memory 84 may be implemented using a database management system (DBMS) and residing on a memory, such as a hard disk, RAM, or removable media. Alternatively, the memory 84 is internal to the processor 82 (e.g. cache).

The instructions for implementing the processes, methods, and/or techniques discussed herein are provided on non-transitory computer-readable storage media or memories, such as a cache, buffer, RAM, removable media, hard drive or other computer readable storage media (e.g., the memory 84). The instructions are executable by the image processor 82 or other processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The medical system 86 is a therapeutic radiation scanner, such as an x-ray or particle therapy system, or a diagnostic imaging scanner, such as CT, MR, PET, or SPECT system. The medical system 86 operates pursuant to one or more settings to treat or image a patient. The settings control the location in the patient being scanned, the type of scan (e.g., pulse sequence), and/or radiation dose. The intensity, frequency, duration, and/or other settings are controlled, at least in part, based on the fit patient model. The patient model may be used to indicate a location on or in the patient, such as a region of interest, an organ location, and/or a center in one, two, or three dimensions. The medical system 86 is configured by setting values of variables to operate in a particular way appropriate for the particular patient as resting on the bed.

In one embodiment, the medical system 86 uses the fit patient model to control a position and/or movement of the bed 89. The bed 89 is configured to be moved based on the fit of the patient model. For example, an organ or region of interest reflected in the fit patient model is used to move the bed 89 so that the actual organ or region of interest of the patient 88 is at an iso-center of the medical system 86. Where the patient 88 then moves, the updated fit using further frames from the sensor 87 may be used to reposition the bed 89 and corresponding organ or region of interest of the patient 88.

Once configured by the settings, the medical system 86 treats or images the patient. For therapy, the amount of radiation applied is based, at least in part, on the fit patient model. For imaging, the medical system 86 is configured to scan an internal region of a patient and generate diagnostic information from the scan. The medical scanner is configured to generate diagnostic image information. The configuration uses settings for one or more parameters, such as an X-ray source voltage, table position and/or range of movement, gantry position and/or range of movement, focus, field of view, scan density, detector thresholds, transmission sequence, image processing settings, filtering settings, or image generation settings. Based on the fit patient model, one or more settings of the medical scanner are automatically or manually set. The patient 88 is imaged by the medical scanner using the settings.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for patient model estimation from surface data in a medical system, the method comprising:
   capturing, with a three-dimensional camera, a stream of the surface data representing an outer surface of a patient at different times including a first time and a second time, the first time earlier than the second time;
   fitting a patient model in a first way to the surface data of the first time;
   monitoring for change in patient position;
   fitting the patient model in a second way to the surface data of the second time, where the second way is different than the first way and uses results of the fitting of the patient model in the first way, the fitting in the second way performed if the patient position is maintained; and
   adjusting a bed position of a bed of the medical system based on the fitting of the patient model in the second way.

2. The method of claim 1 wherein capturing comprises capturing with the three-dimensional camera being a depth sensor.

3. The method of claim 1 wherein fitting the patient model in the first way comprises fitting model landmarks to landmarks detected from the surface data of the first time, and wherein fitting the patient model in the second way comprises fitting a three-dimensional mesh to the surface data of the second time.

4. The method of claim 3 wherein fitting the patient model in the second way using the results comprises initializing the fitting of the three-dimensional mesh from the fitting of the model landmarks to the detected landmarks detected from the surface data of the first time.

5. The method of claim 1 further comprising detecting the patient on the bed from surface data of the stream from an earlier time than the first time, and activating the fitting of the patient model in the first way and the monitoring in response to the detecting of the patient.

6. The method of claim 1 wherein adjusting the bed position comprises adjusting a center of the patient from the patient model fitting in the second way to an iso-center of the medical system.

7. The method of claim 1 wherein capturing and fitting in the first and second ways occur without user input relative to any camera images from the surface data representing the outer surface.

8. The method of claim 1 wherein adjusting comprises adjusting without user input of the bed position.

9. The method of claim 1 wherein the monitoring continues after the fitting to the surface data of the second time;
   further comprising repeating the fitting in the second way using the surface data from a third time after the second time in response to a variation in the patient position, and updating the bed position based on results of the repeating of the fitting in the second way.

10. The method of claim 9 wherein the repeating of the fitting in the second way comprises constraining the fitting in the second way to a region of interest.

11. The method of claim 1 wherein fitting in the second way comprises fitting with constraints for the bed position and constraints for non-patient objects.

12. The method of claim 1 wherein fitting in the first way comprises two-dimensional fitting, and wherein fitting in the second way comprises three-dimensional fitting.

13. The method of claim 1 wherein fitting in the first and second ways comprises three-dimensional fittings.

14. The method of claim 1 further comprising setting scan parameters of the medical system based on the fitting in the second way.

15. The method of claim 1 further comprising signaling a medical professional of completion of the fitting in the first way, of the fitting in the second way, of results of the monitoring, and/or of the adjusting of the bed position.

* * * * *